(12) United States Patent
Terada

(10) Patent No.: US 12,564,379 B2
(45) Date of Patent: Mar. 3, 2026

(54) INTRACAVITARY INSERTION TYPE ULTRASOUND PROBE

(71) Applicant: FUJIFILM Healthcare Corporation, Kashiwa (JP)

(72) Inventor: Takahide Terada, Tokyo (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 18/763,001

(22) Filed: Jul. 3, 2024

(65) Prior Publication Data

US 2025/0057507 A1    Feb. 20, 2025

(30) Foreign Application Priority Data

Aug. 14, 2023    (JP) ................................. 2023-131836

(51) Int. Cl.
 *A61B 8/00*        (2006.01)
 *A61B 8/12*        (2006.01)

(52) U.S. Cl.
 CPC ................ *A61B 8/445* (2013.01); *A61B 8/12* (2013.01); *A61B 8/4488* (2013.01); *A61B 8/56* (2013.01)

(58) Field of Classification Search
 CPC ........................................................ A61B 8/12
 See application file for complete search history.

(56) References Cited

U.S. PATENT DOCUMENTS

| | | | | |
|---|---|---|---|---|
| 2020/0330072 A1* | 10/2020 | Jacobs | ...................... | A61B 8/12 |
| 2021/0045718 A1* | 2/2021 | Moore | ................ | G01S 7/52096 |
| 2021/0338198 A1* | 11/2021 | Wrolstad | ................ | A61B 8/445 |
| 2022/0061805 A1 | 3/2022 | Minas et al. | | |
| 2024/0324996 A1* | 10/2024 | Pellegrino | ............ | A61B 8/4494 |

FOREIGN PATENT DOCUMENTS

| | | |
|---|---|---|
| JP | 2021-505292 A | 2/2021 |
| JP | 2022-516360 A | 2/2022 |
| JP | 2022-544560 A | 10/2022 |

* cited by examiner

*Primary Examiner* — Anh Tuan T Nguyen
*Assistant Examiner* — Tommy T Ly
(74) *Attorney, Agent, or Firm* — Paul Teng

(57)        ABSTRACT

A practically valuable flexible substrate can be provided for an intracavitary insertion type ultrasound probe. A flexible substrate includes a substrate main body and a plurality of tabs. The substrate main body is provided with a transducer array and a plurality of electronic components (ICs). In a state where the flexible substrate is rolled into a tubular shape, one end and the other end of the substrate main body in a circumferential direction come into contact with each other or come close to each other. A first tab is provided with a first connection to which a first cable group is connected. A second tab is provided with a second connection to which a second cable group is connected.

6 Claims, 9 Drawing Sheets

INTRACAVITARY INSERTION TYPE ULTRASOUND PROBE

CROSS REFERENCE TO RELATED APPLICATION

The present application claims priority from Japanese Patent Application No. 2023-131836, filed on Aug. 14, 2023, the content of which is hereby incorporated by reference into this application.

BACKGROUND OF THE INVENTION

1. Field of the Invention

The present disclosure relates to an intracavitary insertion type ultrasound probe, and particularly to a flexible substrate that is rolled into a tubular shape.

2. Description of the Related Art

As the intracavitary insertion type ultrasound probe, a small diameter probe such as an intravascular ultrasound (IVUS) probe is known. Such a probe is also referred to as a catheter type ultrasound probe.

In an electronic scanning IVUS probe of the related art, a flexible printed circuit (FPC) substrate rolled into a tubular shape is disposed in a tip part of the electronic scanning IVUS probe (hereinafter, the FPC substrate will be simply referred to as a flexible substrate). The flexible substrate is provided with a transducer array and a plurality of electronic components. Specifically, the plurality of electronic components are a plurality of integrated circuits (ICs). Further, the flexible substrate is provided with a plurality of connections. Each connection consists of, for example, a plurality of electrodes or a plurality of terminals to which a plurality of cables are connected.

The flexible substrate has a wiring pattern. The wiring pattern includes a line group that connects the plurality of electronic components to the transducer array and a line group that connects the plurality of electronic components to the plurality of connections. The plurality of connections are usually a part of the wiring pattern. The plurality of cables are connected to the plurality of connections before the flexible substrate is rolled or after the flexible substrate is rolled.

JP2021-505292A discloses an electronic scanning IVUS probe. More specifically, FIG. 2 of JP2021-505292A shows a flexible substrate comprising a transducer array and a plurality of ICs. The flexible substrate includes a substrate main body and one tab. The tab comprises a connection. FIG. 5 of JP2021-505292A shows a substrate main body and a flexible substrate having a plurality of ribbons. An electronic component is mounted on each ribbon. An electronic component is not mounted on the substrate main body. JP2021-505292A does not disclose a plurality of tabs corresponding to a plurality of wiring line systems crossing a plurality of electronic components.

SUMMARY OF THE INVENTION

An object of the present disclosure is to provide a practically valuable flexible substrate for an intracavitary insertion type ultrasound probe. Alternatively, an object of the present disclosure is to realize a functional tab array and a functional wiring pattern. Alternatively, an object of the present disclosure is to facilitate an assembly work of an intracavitary insertion type ultrasound probe.

An intracavitary insertion type ultrasound probe according to the present disclosure comprises a flexible substrate including a substrate main body that is rolled into a tubular shape and a plurality of tabs that are connected to an annular rear end of the substrate main body, an annular transducer array that is provided on the substrate main body, and a plurality of electronic components that are provided on the substrate main body, are electrically connected to the transducer array, and are disposed side by side annularly, in which one end and the other end of the substrate main body in a circumferential direction are in contact with or close to each other, the substrate main body includes one end part including the one end and the other end part including the other end, the plurality of tabs include a first tab connected to the one end part and a second tab connected to the other end part, the first tab is provided with a first connection to which a first cable group is connected, and the second tab is provided with a second connection to which a second cable group is connected.

According to the present disclosure, it is possible to provide the practically valuable flexible substrate. Alternatively, according to the present disclosure, it is possible to realize the functional tab array and the functional wiring pattern. Alternatively, according to the present disclosure, it is possible to facilitate the assembly work of the intracavitary insertion type ultrasound probe.

DESCRIPTION OF THE PREFERRED EMBODIMENTS

Figure 1:
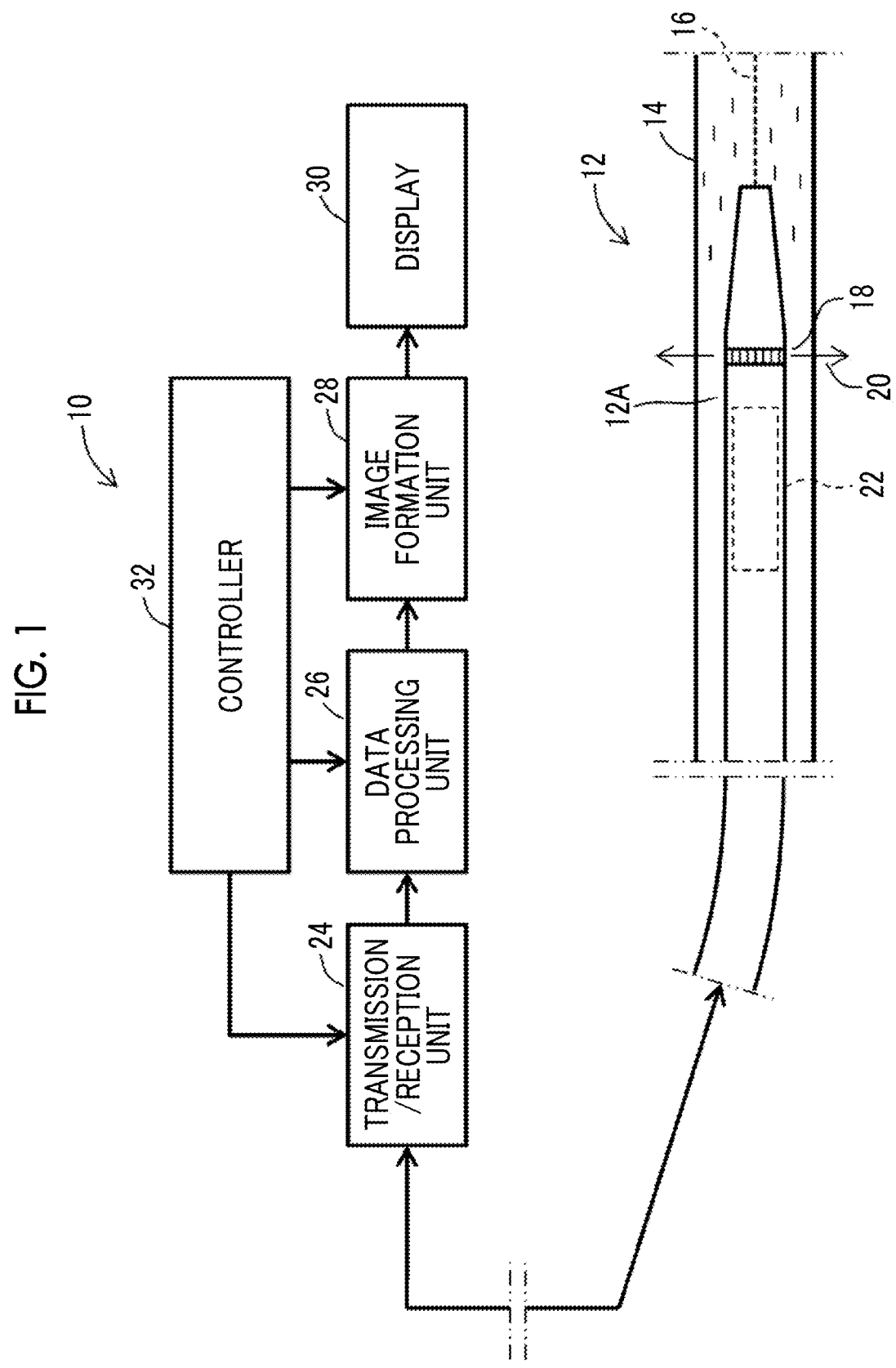
FIG. 1 is a schematic diagram showing a configuration example of an ultrasound diagnostic apparatus according to an embodiment.

Hereinafter, an embodiment will be described with reference to the accompanying drawings.

(1) Outline of Embodiment

An intracavitary insertion type ultrasound probe according to an embodiment includes a flexible substrate, a transducer array, and a plurality of electronic components. The flexible substrate includes a substrate main body that is rolled into a tubular shape, and a plurality of tabs that are connected to an annular rear end of the substrate main body. The transducer array has an annular form, and is provided on the substrate main body. The plurality of electronic components are provided on the substrate main body, and specifically, the plurality of electronic components are disposed side by side annularly on the substrate main body. The plurality of electronic components are electrically connected to the transducer array. In a case where the flexible substrate is rolled into the tubular shape, one end and the other end of the substrate main body in a circumferential direction come into contact with each other or come close to each other. The substrate main body includes one end part including one end and the other end part including the other end. The plurality of tabs include a first tab that is connected to one end part and a second tab that is connected to the other end part. The first tab is provided with a first connection to which a first cable group is connected. The second tab is provided with a second connection to which a second cable group is connected.

In the embodiment, the plurality of electronic components are configured of a first electronic component to an m-th electronic component. Here, m is an integer of 2 or more, and for example, m is in a range of 4 to 8. The m electronic components are connected to each other, for example, via one or a plurality of cross line arrays. The first electronic component is provided at a location (one end part) close to one end of the substrate main body, and the m-th electronic component is provided at a location (the other end part) close to the other end of the substrate main body. On the premise of such a layout, with the flexible substrate according to the embodiment, the first connection can be brought close to the first electronic component, and the second connection can be brought close to the m-th electronic component at the same time. Accordingly, it is possible to shorten a total wiring length of the wiring pattern on the flexible substrate, or simplify the wiring pattern.

The substrate main body may be provided with three or more tabs. In a case where a width of the tab in the circumferential direction is increased, it is difficult to bend the tab. Thus, the width of the tab in the circumferential direction is decided in consideration of the necessity of bending or the ease of bending work. In a state where the flexible substrate is rolled into the tubular shape, the first tab and the second tab are adjacent to each other. That is, the first connection and the second connection come close to each other. In order to reduce electrical crosstalk or to prevent noise from being mixed into a reception signal, a member that exerts a shielding action is provided between the first connection and the second connection. The first connection and the second connection are each configured of one or a plurality of electrodes or one or a plurality of terminals.

In the embodiment, the flexible substrate includes a first cross line array, a second cross line array, a first peripheral line array, and a second peripheral line array. The first cross line array extends from one end part to the other end part of the flexible substrate and is electrically connected to the plurality of electronic components. The second cross line array extends from the other end part to one end part of the flexible substrate and is electrically connected to the plurality of electronic components. The first peripheral line array is provided between the first cross line array and the first connection. The second peripheral line array is provided between the second cross line array and the second connection.

A first wiring line system is configured of the first cross line array and the first peripheral line array, and a second wiring line system is configured of the second cross line array and the second peripheral line array. With the above configuration, an intersection between the two wiring line systems can be avoided.

In the embodiment, the first cross line array and the first peripheral line array each include a plurality of lines for transmitting a plurality of reception signals. The second cross line array and the second peripheral line array each include a line for transmitting a control signal and a line for supplying a power voltage. With the above configuration, it is possible to prevent or reduce the mixing of noise into each reception signal on the flexible substrate.

In the embodiment, the flexible substrate includes a ground line provided between the first connection and the second connection. With the above configuration, it is possible to reduce the electrical crosstalk between the first connection and the second connection.

In the embodiment, the plurality of reception signals are transmitted via the first connection. The first tab includes the ground line surrounding the first connection. With the above configuration, it is possible to prevent or reduce the mixing of noise into each reception signal.

In the embodiment, the substrate main body has a first region, a second region, and a third region. The first region is provided with the transducer array. The second region is a region provided on a rear side of the first region, and the second region is provided with the plurality of electronic components. The third region is a region between the second region and the annular rear end. Each tab is extended in parallel to a probe central axis direction in a normal state. In a case where a pressing force is applied to each tab toward an outer side in a radial direction, the third region is deformed. Accordingly, each tab is allowed to be bent. The third region is a margin region or a redundant region. With the presence of the third region, each tab is allowed to be bent or each tab is easily bent.

In the embodiment, at least one of the plurality of tabs includes a tab main body and a coupling part provided between the tab main body and the substrate main body. A width of a boundary between the coupling part and the substrate main body is smaller than a width of the tab main body in the circumferential direction. With the above configuration, the tab is easily bent.

(2) Details of Embodiment

FIG. 1 shows an ultrasound diagnostic apparatus according to the embodiment. The ultrasound diagnostic apparatus is used in an ultrasound examination of a living body (human). The ultrasound diagnostic apparatus includes an apparatus main body 10 and an intracavitary insertion type ultrasound probe (hereinafter referred to as probe) 12. Specifically, the probe 12 is an electronic scanning IVUS probe to be inserted into a blood vessel 14. A configuration described below may be applied to another probe (for example, ultrasonic endoscope for bronchus).

The probe 12 is a long member having flexibility. An outer diameter of the probe 12 is, for example, in a range of 1 to 3 mm. The outer diameter of the probe 12 may be in the range thereof or less or in the range thereof or more.

A tip part 12A of the probe 12 has a transducer array 18 having an annular form. The transducer array 18 is configured of, for example, a plurality of transducers arranged annularly. A transmission opening and the reception opening are set on the transducer array 18. An ultrasound wave is radiated from the transmission opening, and a reflected wave is received by the reception opening. An ultrasound beam (transmission/reception integrated beam) 20 is radially scanned by the electronic scanning of the openings.

An electronic component group 22 is provided in the tip part 12A. The electronic component group 22 is electrically connected to the transducer array 18. The transmission opening and the reception opening are subjected to electronic scanning by an action of the electronic component group 22. The electronic component group 22 is configured of the plurality of electronic components. The number of electronic components is, for example, in a range of 4 to 8, and may be 5 or 6. Each electronic component is configured of, for example, an application specific integrated circuit (ASIC).

The probe 12 has a hollow passage formed along a central axis thereof. A guide wire 16 is inserted into the passage. More accurately, the probe 12 advances in the blood vessel 14 along the guide wire 16 that is already disposed in the blood vessel 14.

The transmission/reception unit 24 is an electronic circuit that functions as a transmission control circuit and also functions as a reception beam former. Transmission/reception control data is transmitted from the transmission/reception unit 24 to the electronic component group 22. The electronic component group 22 generates a plurality of transmission signals at the time of transmission. The transmission signals are transmitted to the transducer array 18. With the transmission, a transmission beam is formed by the transducer array 18.

During the reception, the plurality of reception signals output in parallel from the transducer array 18 are transmitted to the transmission/reception unit 24 via the electronic component group 22. In the transmission/reception unit 24, coherent addition is applied to the plurality of reception signals. With the coherent addition, reception beam data is generated. Sub-beam forming for reception may be performed in the electronic component group 22.

Although an interface unit is provided between the probe 12 and the transmission/reception unit 24, an illustration thereof is omitted in FIG. 1. A plurality of pieces of reception beam data are sequentially transmitted from the transmission/reception unit 24 to an image formation unit 28 via a data processing unit 26 as the ultrasound beam 20 is radially scanned.

The data processing unit 26 includes a detection circuit, a filter circuit, a logarithmic conversion circuit, and the like. The image formation unit 28 is configured of a digital scan converter (DSC). A tomographic image is formed from the plurality of pieces of reception beam data by the DSC. The tomographic image is displayed on a display 30. The tomographic image is, for example, a motion picture image showing a transverse cross section of the blood vessel 14. A motion picture image representing a longitudinal cross section of the blood vessel may be displayed on the display 30. In that case, a plurality of pieces of transverse cross section data may be connected in a blood vessel central axis direction to generate the tomographic image representing the longitudinal cross section of the blood vessel. A three-dimensional image may be displayed on the display 30.

A controller 32 has a central processing unit (CPU) that executes a program. The controller 32 controls an operation of each component in the ultrasound diagnostic apparatus. The display 30 is configured of an organic EL display device, a liquid crystal display (LCD), or the like. An operation panel (not shown) is connected to the controller 32.

Figure 2:
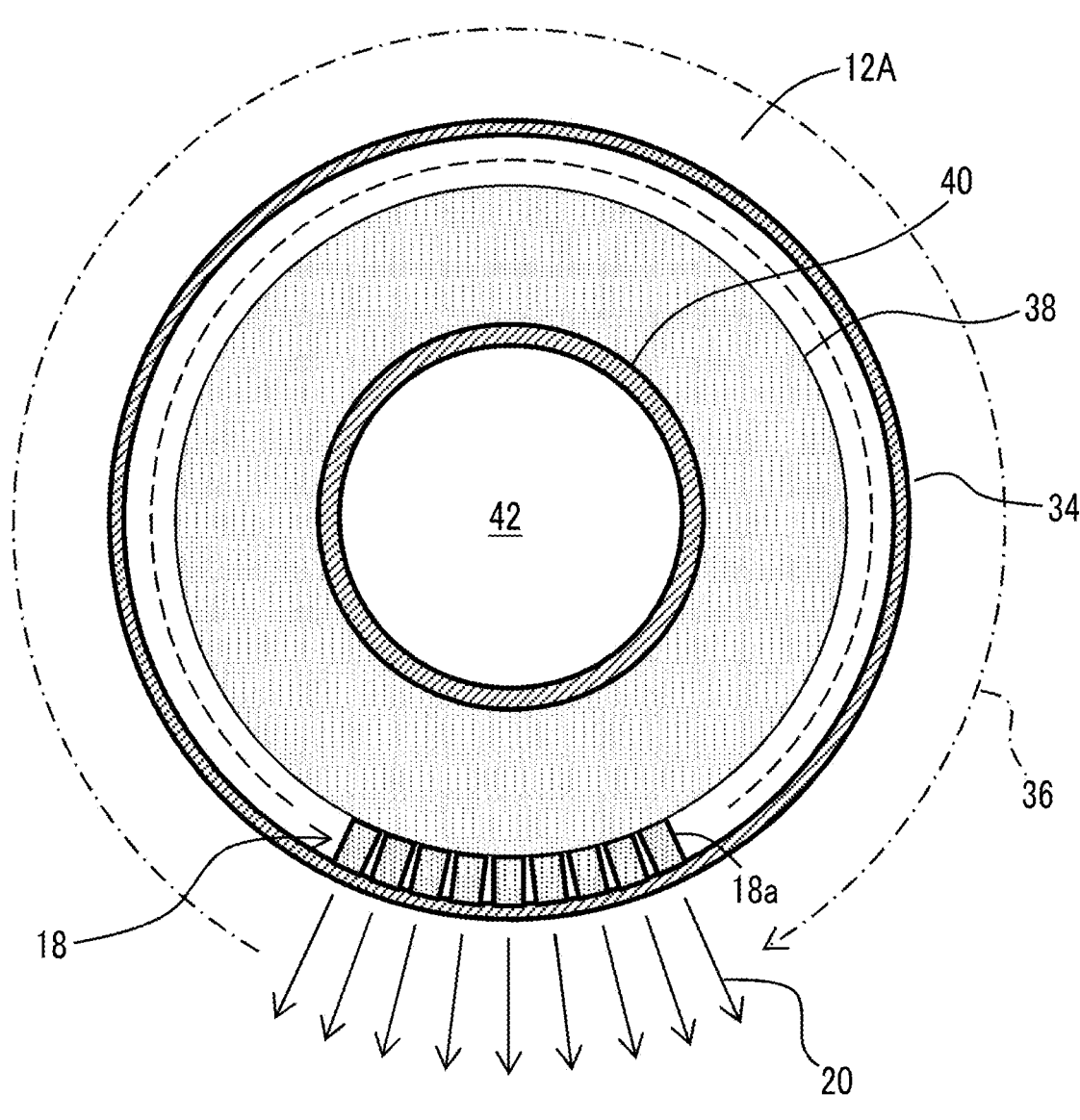
FIG. 2 is a cross-sectional view of a tip part.

FIG. 2 shows a cross section of the probe according to the embodiment. Specifically, FIG. 2 shows a schematic view of a transverse cross section of the tip part 12A. A flexible substrate 34 is a film member for wiring having flexibility, which is configured of an FPC. The flexible substrate 34 has an annular form. The transducer array 18 is provided on an inner side of the flexible substrate 34. The transducer array 18 is configured of a plurality of transducers 18a disposed annularly. The ultrasound wave transmitted from each transducer 18a is transmitted through the flexible substrate 34 and then radiated into the living body. The reflected wave from the living body is transmitted through the flexible substrate 34 and then received by each transducer 18a. The ultrasound beam 20 is radially scanned as shown in the drawing (refer to reference numeral 36).

A cylindrical backing 38 is provided on an inner side of the transducer array 18. The backing 38 is a member that attenuates the ultrasound wave radiated rearward from each transducer 18a. A pipe 40 is provided on an inner side of the backing 38. An inside of the pipe 40 is a passage 42 into which the guide wire is inserted.

Figure 3:
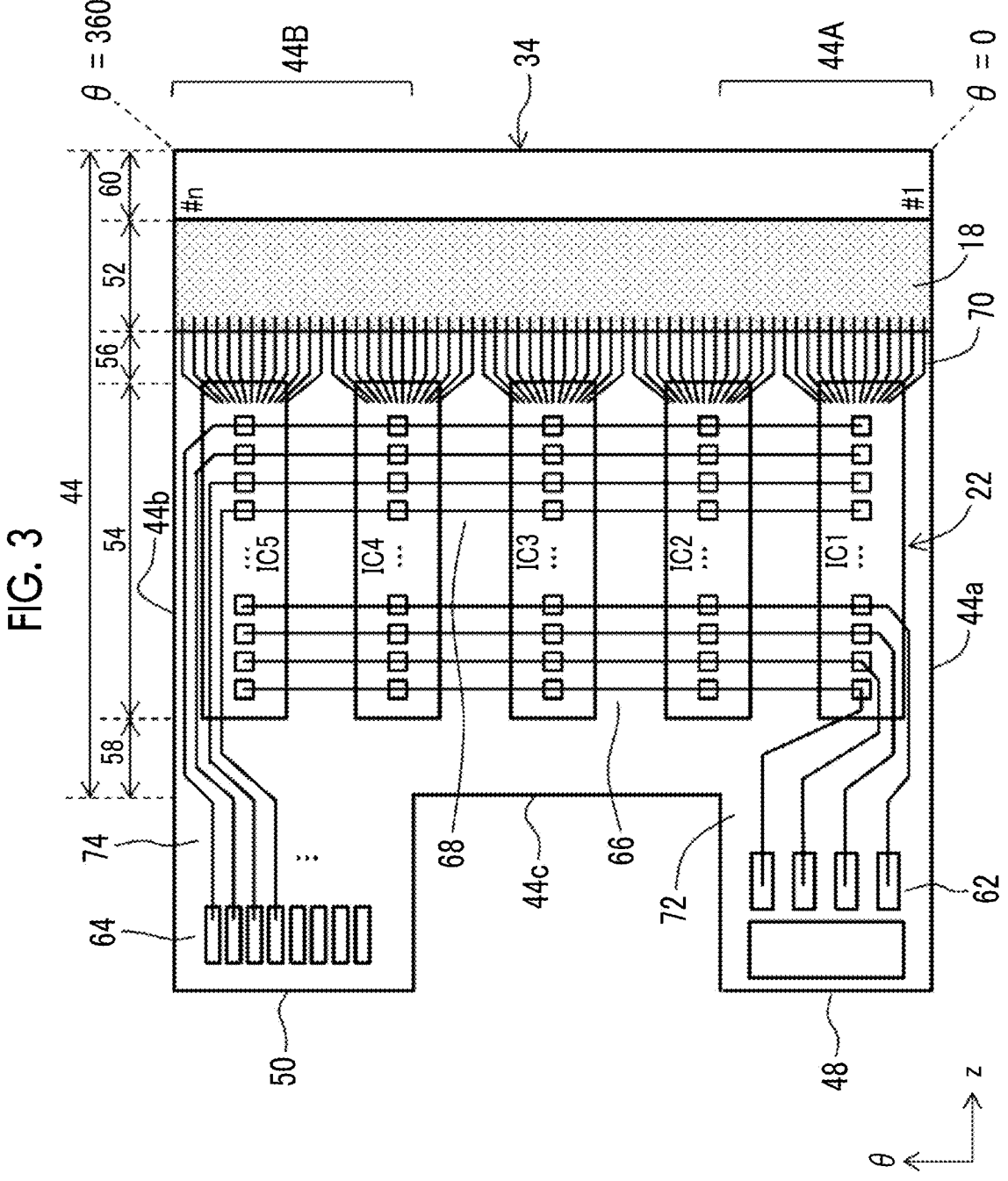
FIG. 3 is a developed view of a first example of a flexible substrate.

A first example of the flexible substrate will be specifically described with reference to FIGS. 3 to 5. FIG. 3 shows the flexible substrate 34 in a development state. A z direction is a direction parallel to a probe central axis. A θ direction is the circumferential direction. The flexible substrate 34 is a thin sheet-like member, and specifically, is an FPC. The flexible substrate 34 consists of a substrate main body 44, a first tab 48, and a second tab 50.

The substrate main body 44 has a rectangular form in the development state and is rolled into the tubular shape at a time of probe assembly. A surface of the flexible substrate 34 shown in FIG. 3 is an inner surface at the time of probe assembly. A reference numeral 44a indicates one end of the substrate main body 44 in the θ direction, and a reference numeral 44b indicates the other end of the substrate main body 44 in the θ direction. The substrate main body 44 has one end part 44A including the one end 44a and has the other end part 44B including the other end 44b.

The first tab 48 and the second tab 50 are connected to a rear end 44c of the substrate main body 44. Specifically, the first tab 48 is connected to the one end part 44A, and the second tab 50 is connected to the other end part 44B. In other words, a portion where the first tab 48 is connected is the one end part 44A, and a portion where the second tab 50 is connected is the other end part 44B. At the time of probe assembly, the one end 44a and the other end 44b come into contact with each other or come close to each other, and the rear end 44c is annular. In other words, the substrate main body 44 is rolled into the tubular shape such that the one end 44a and the other end 44b come into contact with each other or come close to each other.

The first tab 48 is provided with a first connection 62, and the second tab 50 is provided with a second connection 64. A first cable group is connected to the first connection 62, and a second cable group is connected to the second connection 64. Each of the connections 62 and 64 includes the plurality of electrodes for soldering connection. The plurality of terminals may be provided together with the plurality of electrodes or instead of the plurality of electrodes.

The transducer array 18 and the electronic component group 22 are provided on the substrate main body 44. More specifically, the substrate main body 44 has a disposition region (first region) 52 and a disposition region (second region) 54. The transducer array 18 is provided on the disposition region 52, and the electronic component group 22 is provided on the disposition region 54. The transducer array 18 is configured of the plurality of transducers disposed side by side in the θ direction. Specifically, the transducer array 18 consists of a first transducer to an n-th transducer. n is, for example, several tens or several hundreds.

The electronic component group 22 is configured of m electronic components. m is an integer of 2 or more, and for example, m is in a range of 4 to 8. In FIG. 3, the electronic component group 22 is configured of five electronic components (IC1 to IC5) disposed side by side in the θ direction. That is, m=5. Each of the electronic components (IC1 to IC5) has a form extending in the z direction.

The substrate main body 44 includes the wiring pattern. The wiring pattern includes a first cross line array 66, a second cross line array 68, a first peripheral line array 72, and a second peripheral line array 74. In the embodiment, the wiring pattern further includes a plurality of connections 62 and 64.

The first cross line array 66 is provided from the one end part 44A to the other end part 44B to cross the five electronic components (IC1 to IC5). The first cross line array 66 is configured of a plurality of lines parallel to the θ direction. Each line is electrically connected to each of the electronic components (IC1 to IC5). In the embodiment, the first cross line array 66 includes four lines for parallel transmission of four reception signals.

The second cross line array 68 is provided from the other end part 44B to the one end part 44A to cross the five electronic components (IC1 to IC5). The second cross line array 68 is configured of a plurality of lines parallel to the θ direction. Each line is electrically connected to each of the electronic components (IC1 to IC5). In the embodiment, the second cross line array 68 includes a line for transmitting the control signal, a line for transmitting a clock, and a plurality of lines for supplying the power voltage. The first cross line array 66 and the second cross line array 68 are separated from each other in the z direction, and a line intersection does not occur therebetween.

The first peripheral line array 72 is connected to the first cross line array 66. The number of lines constituting the first peripheral line array 72 is the same as the number of lines constituting the first cross line array 66. The first peripheral line array 72 is formed from the one end part 44A to the first tab 48. Specifically, the one end part of the first cross line array 66 and the first connection 62 are electrically connected to each other by the first peripheral line array 72. The line intersection does not occur in the first peripheral line array 72. The first connection 62 is configured of the plurality of electrodes. More specifically, the first connection 62 is configured of the plurality of electrodes to which a plurality of internal conductors in a plurality of coaxial cables are connected, and a ground electrode to which a plurality of external conductors in the plurality of coaxial cables are connected.

The second peripheral line array 74 is connected to the second cross line array 68. The number of lines constituting the second peripheral line array 74 is the same as the number of lines constituting the second cross line array 68. The second peripheral line array 74 is formed from the other end part 44B to the second tab 50. Specifically, the other end part of the second cross line array 68 and the second connection 64 are electrically connected to each other by the second peripheral line array 74. The line intersection does not occur in the second peripheral line array 74. The second connection 64 is configured of the plurality of electrodes. More specifically, the second connection 64 is configured of the plurality of electrodes to which a plurality of conductors in the plurality of cables are connected. In FIG. 3, a part of lines is not shown.

The substrate main body 44 has a front-side margin region 60, an intermediate wire region 56, and a rear-side margin region (third region) 58. A line array 70 for electrically connecting the electronic component group 22 and the transducer array 18 is provided in the intermediate wire region 56. The line array 70 is a part of the above wiring pattern.

The rear-side margin region 58 is a region between the electronic component group 22 and the rear end 44c. The rear-side margin region 58 is the redundant region. With the provision of the rear-side margin region 58, the first tab 48 and the second tab 50 are allowed to be bent toward the outer side in the radial direction in a state where the substrate main body 44 is rolled into the tubular shape. For example, in a case where a diameter of the substrate main body 44 is denoted by L in a case where the substrate main body 44 is rolled, a width of the rear-side margin region 58 in the z direction may be L/2 or more. For example, the width thereof may be 2 L or less. By the way, a width of each tab in the θ direction may be ⅔×L or more and L or less. In a case where the flexible substrate 34 is processed, rounded processing is performed on each corner portion included in the flexible substrate 34.

With the flexible substrate 34 shown in FIG. 3, the following advantages can be obtained. First, since the first tab 48 connected to the one end part 44A and the second tab 50 connected to the other end part 44B are provided on the premise that the first cross line array 66 and the second cross line array 68 are provided, it is possible to shorten the total wiring length of the wiring pattern, or simplify the wiring pattern.

Second, since the first wiring line system (the first cross line array 66 and the first peripheral line array 72) and the second wiring line system (the second cross line array 68 and the second peripheral line array 74) are separated in an orderly manner, it is possible to prevent or reduce the electrical crosstalk. In particular, it is possible to prevent or reduce the mixing of noise into the reception signal on the flexible substrate 34.

Third, since the rear-side margin region 58 is provided and another tab is not provided between the two tabs 48 and 50, each of the tabs 48 and 50 is likely to be bent toward the outer side in the radial direction at the time of probe assembly.

Figure 4:
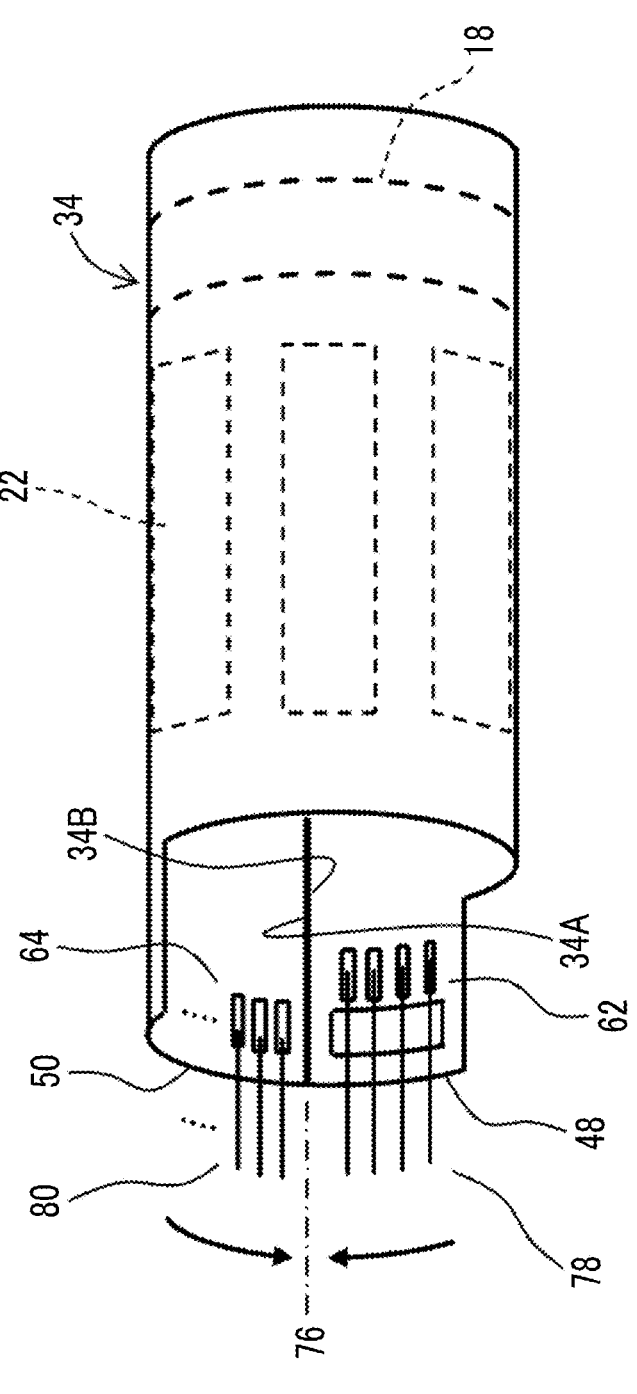
FIG. 4 is a perspective view of the first example of the flexible substrate.

FIG. 4 shows the flexible substrate 34 that is rolled into the tubular shape. One end 34A and the other end 34B of the flexible substrate 34 are in contact with or close to each other. A reference numeral 76 indicates a boundary between the one end 34A and the other end 34B. The transducer array 18 and the electronic component group 22 are provided on an inner surface of the substrate main body. At a position where the transducer array 18 is provided, a cross-sectional shape of the flexible substrate 34 is close to a circular shape. At a position where the electronic component group 22 is provided, the cross-sectional shape of the flexible substrate 34 is close to a polygonal shape.

The first connection 62 is provided on an inner surface of the first tab 48, and a first cable group 78 is connected to the first connection. In the example shown in the drawing, each cable constituting the first cable group 78 is a coaxial cable. The second connection 64 is provided on an inner surface of the second tab 50. A second cable group 80 is connected to the second connection 64. In the example shown in the drawing, each cable constituting the second cable group 80 is a non-coaxial cable.

Figure 5:
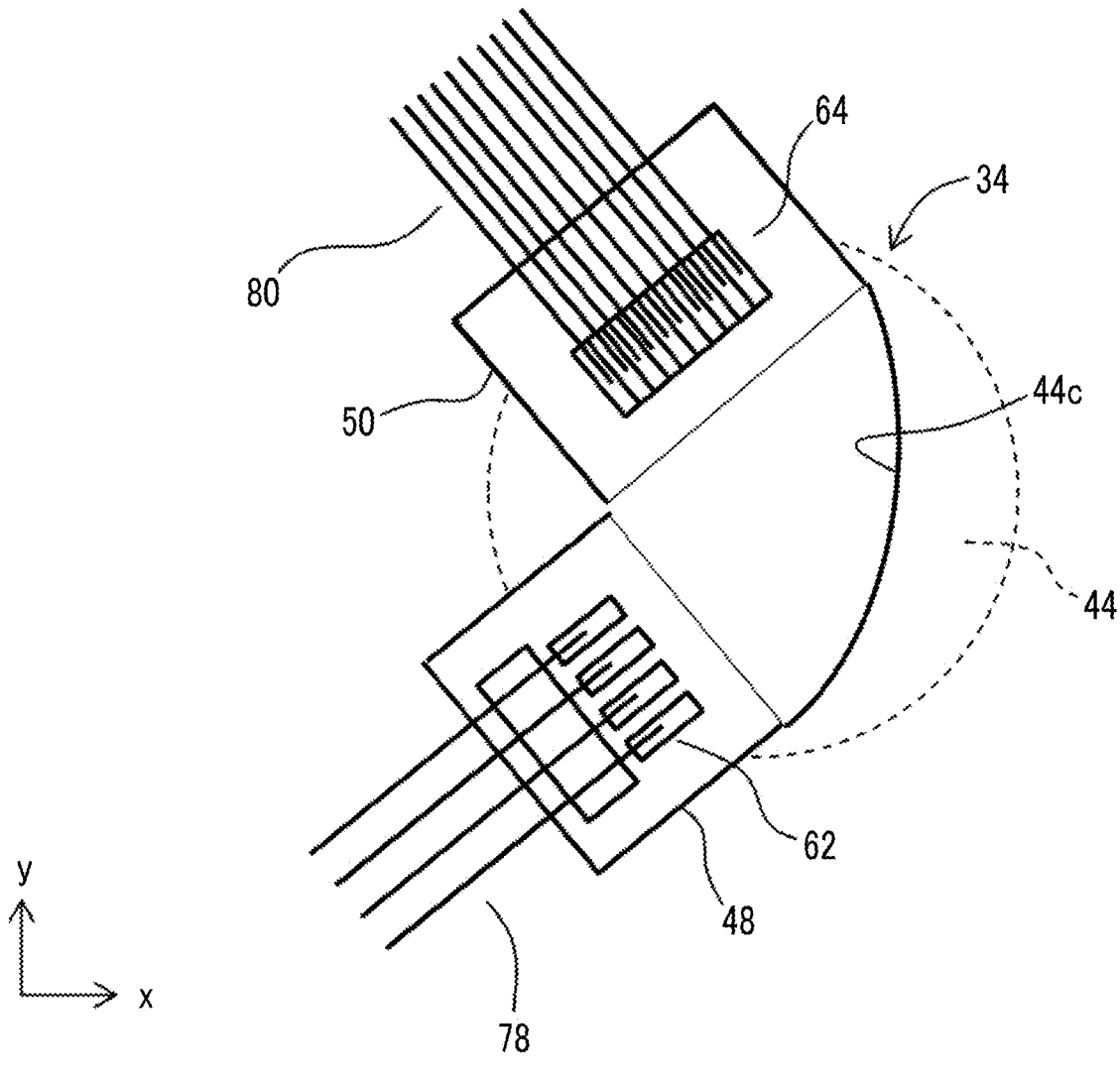
FIG. 5 is a diagram showing a state where a tab is bent.

FIG. 5 shows a rear end part of the flexible substrate 34. An x direction and a y direction are directions orthogonal to the probe central axis (z direction). The first tab 48 and the second tab 50 are bent with respect to the substrate main body 44. The reference numeral 44c indicates the rear end of the substrate main body.

In the state shown in the drawing, the first cable group 78 is connected to the first connection 62 on the first tab 48, and the second cable group 80 is connected to the second connection 64 on the second tab 50. The first cable group 78 and the second cable group 80 may be connected before the flexible substrate 34 is rolled. The first cable group 78 and the second cable group 80 may be connected to each other in stages while the first tab 48 and the second tab 50 are bent in order.

Figure 6:
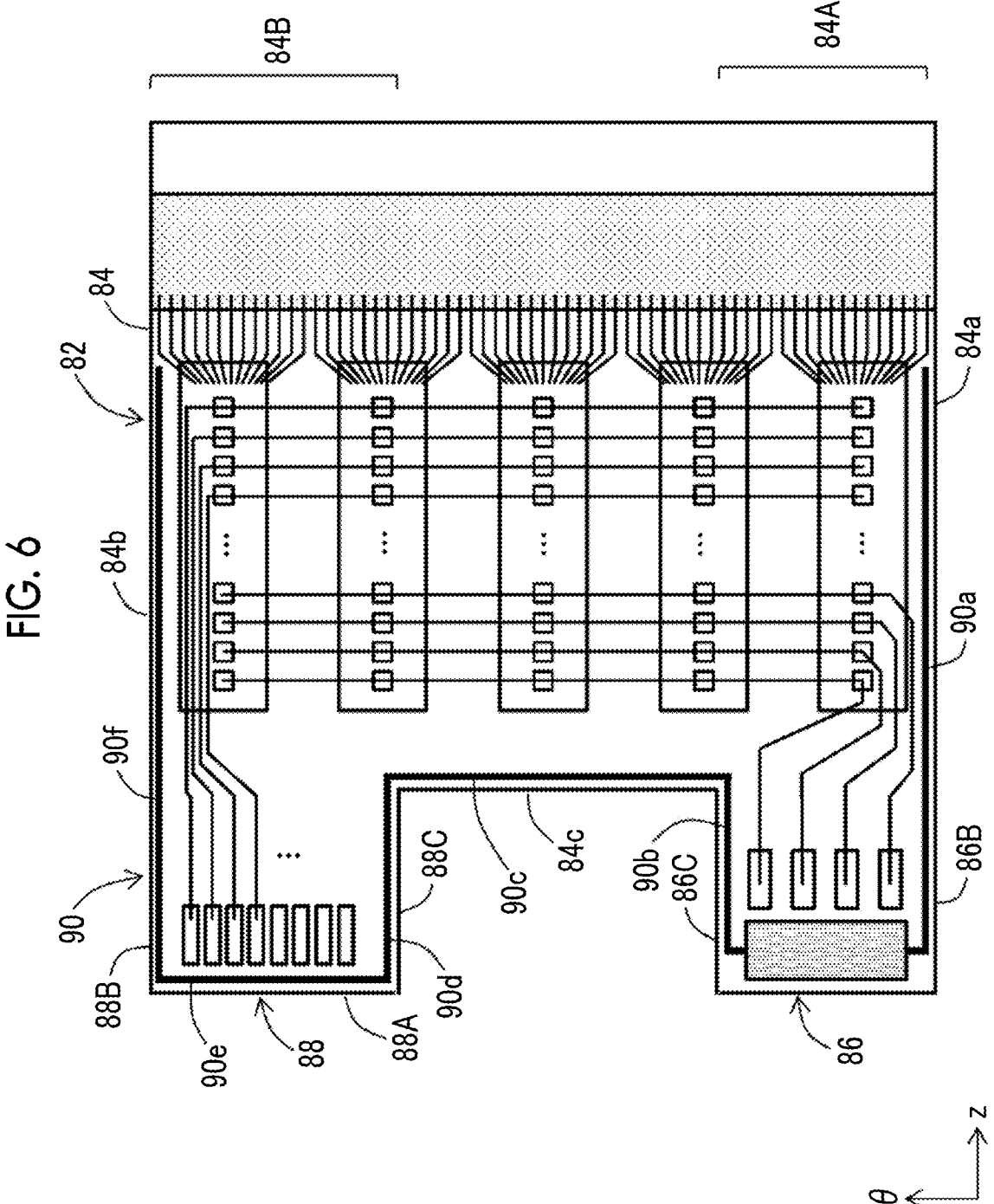
FIG. 6 is a developed view of a second example of the flexible substrate.

FIG. 6 shows a second example of the flexible substrate. The flexible substrate 82 shown in the drawing includes a substrate main body 84, a first tab 86, and a second tab 88. The substrate main body 84 includes one end part 84A and the other end part 84B. The first tab 86 is connected to the one end part 84A, and the second tab 88 is connected to the other end part 84B. The first tab 86 has side surfaces 86B and 86C, and the second tab 88 has side surfaces 88A, 88B, and 88C.

The wiring pattern includes a ground pattern 90. In the illustrated configuration example, the ground pattern 90 consists of a first portion 90*a*, a second portion 90*b*, a third portion 90*c*, a fourth portion 90*d*, a fifth portion 90*e*, and a sixth portion 90*f*.

The first portion 90*a* is a ground line formed along the one end 84*a* of the substrate main body 84 and the side surface 86B of the first tab 86. The second portion 90*b* is a ground line formed along the side surface 86C of the first tab 86. The third portion 90*c* is a ground line formed along a rear end 84*c* of the substrate main body 84. The fourth portion 90*d* is a ground line formed along the side surface 88C of the second tab 88. The fifth portion 90*e* is a ground line formed along the side surface 88A of the second tab 88. The sixth portion 90*f* is a ground line formed along the side surface 88B of the second tab 88 and the other end 84*b* of the substrate main body 84.

An end part of the first portion 90*a* and an end part of the second portion 90*b* are connected to the ground electrode in the first connection. A plurality of signal electrodes in the first connection are surrounded by the ground line. The second connection is also surrounded by the ground line.

According to the second example described above, since a ground member is provided between the first connection and the second connection in a state where the flexible substrate 82 is rolled into the tubular shape, and the ground member is provided between the first peripheral line group and the second peripheral line group, it is possible to prevent or reduce the electrical crosstalk. Further, since the ground line is provided around the wiring pattern, it is possible to reduce noise mixed into the reception signal.

Figure 7:
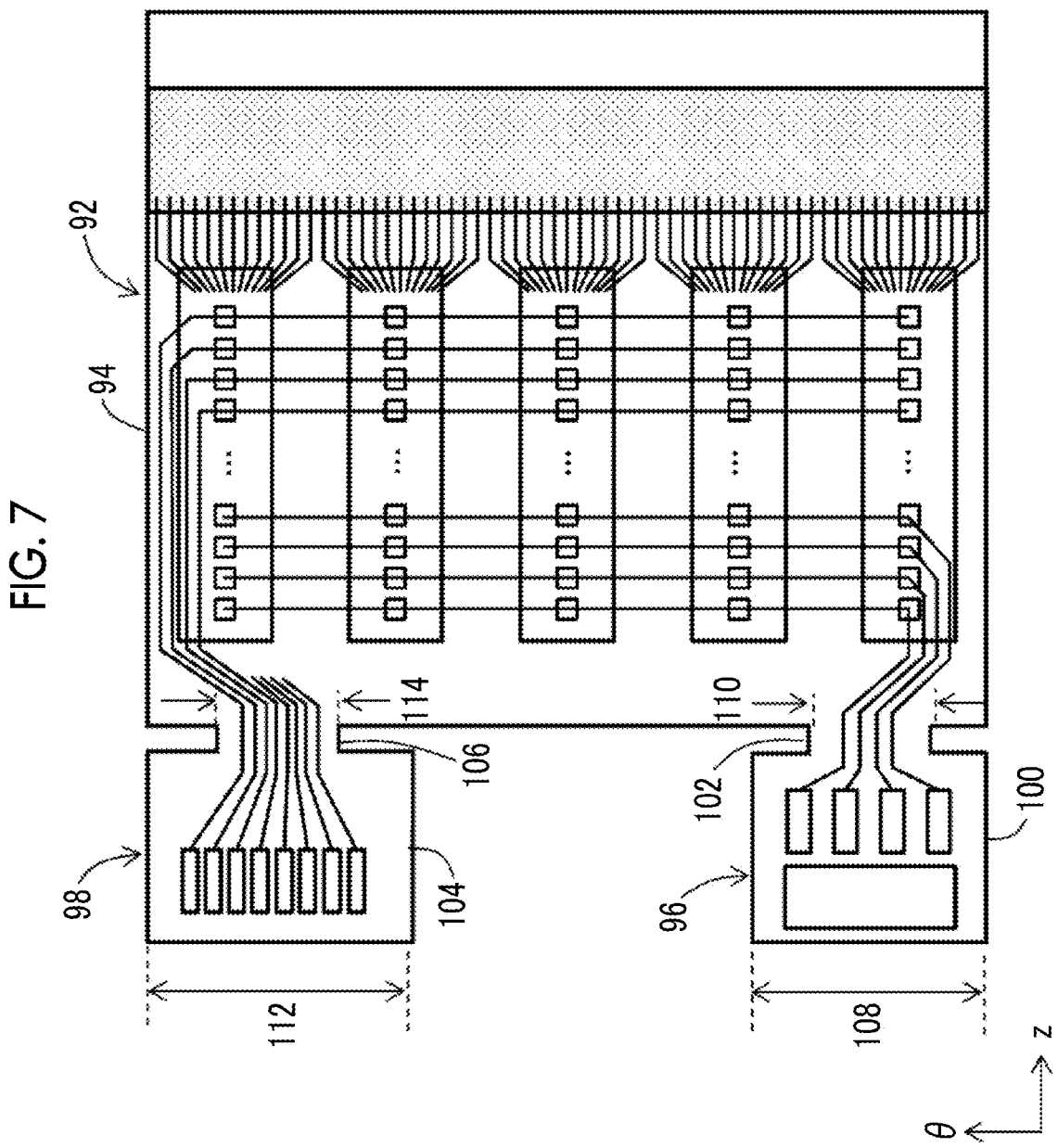
FIG. 7 is a developed view of a third example of the flexible substrate.

FIG. 7 shows a third example of the flexible substrate. In a flexible substrate 92, a first tab 96 and a second tab 98 are connected to one end part and the other end part of a substrate main body 94, respectively. The first tab 96 consists of a tab main body 100 and a coupling part 102. The second tab 98 also consists of a tab main body 104 and a coupling part 106.

The tab main bodies 100 and 104 are swollen. The coupling parts 102 and 106 correspond to a constricted portion. Specifically, a width 110 of the coupling part 102 in the θ direction is smaller than a width 108 of the tab main body 100 in the θ direction. A width 114 of the coupling part 106 in the θ direction is smaller than a width 112 of the tab main body 104 in the θ direction. In a case where sizes of the widths 110 and 114 are decided, the ease of bending and the number of lines passing through the coupling parts 102 and 106 are considered. In any case, according to the third example shown in FIG. 7, in a state where the flexible substrate 92 is rolled into the tubular shape, the two tabs 96 and 98 are likely to be bent toward the outer side in the radial direction.

Figure 8:
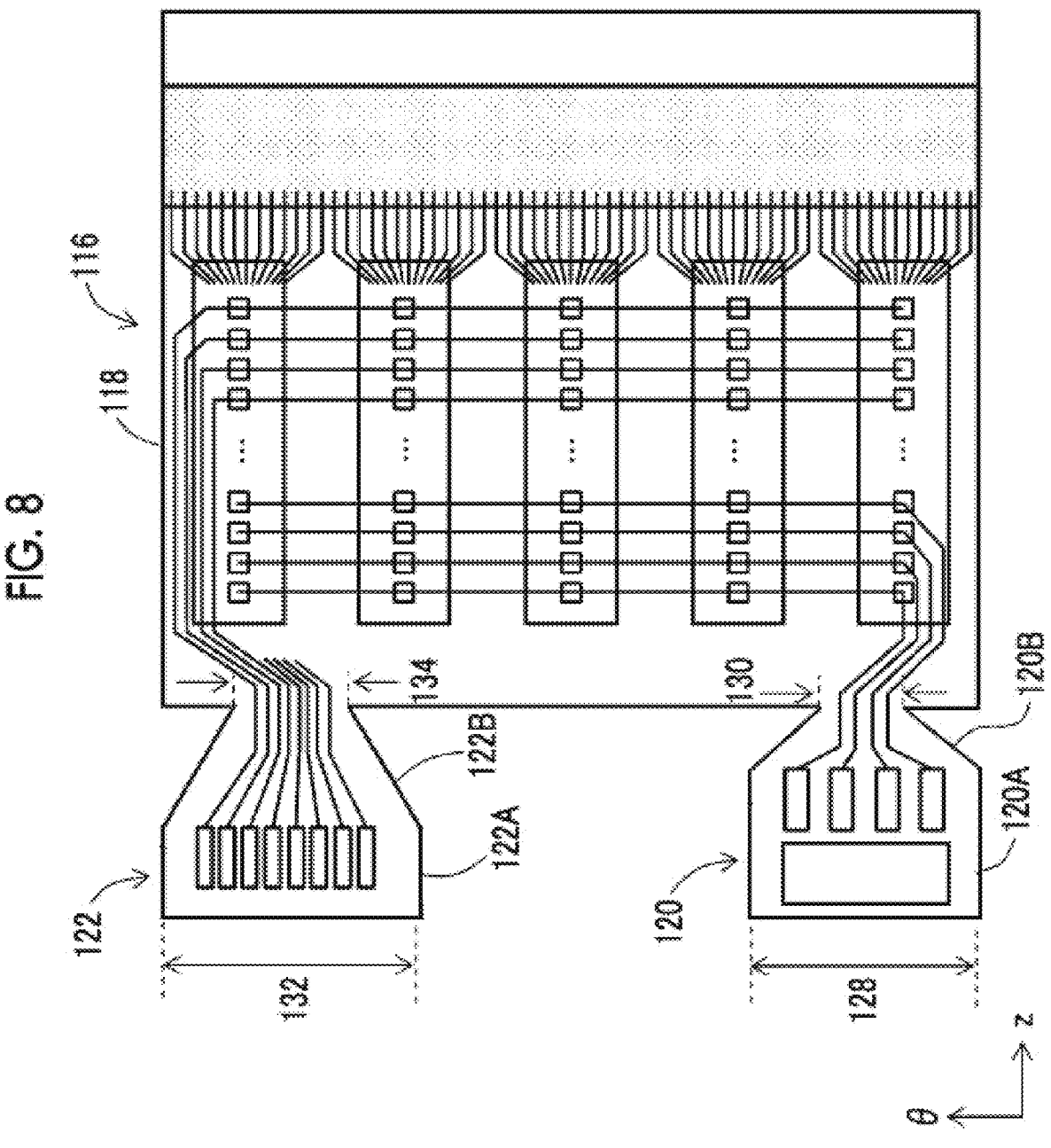
FIG. 8 is a developed view of a fourth example of the flexible substrate.

FIG. 8 shows a fourth example of the flexible substrate. In a flexible substrate 116, a first tab 120 and a second tab 122 are connected to one end part and the other end part of a substrate main body 118, respectively. The first tab 120 consists of a tab main body 120A and a coupling part 120B. The second tab 122 also consists of a tab main body 122A and a coupling part 122B. The coupling parts 120B and 122B each have a trapezoidal form. That is, the coupling parts 120B and 122B each have a tapered form.

Specifically, a width (boundary width) 130 of a distal end of the coupling part 120B in the θ direction is smaller than a width 128 of the tab main body 120A in the θ direction. A width (boundary width) 134 of a distal end of the coupling part 122B in the θ direction is smaller than a width 132 of the tab main body 122A in the θ direction. According to the fourth example shown in FIG. 8, similarly to the third example, in a state where the flexible substrate 116 is rolled into the tubular shape, the two tabs 120 and 122 are likely to be bent toward the outer side in the radial direction.

Figure 9:
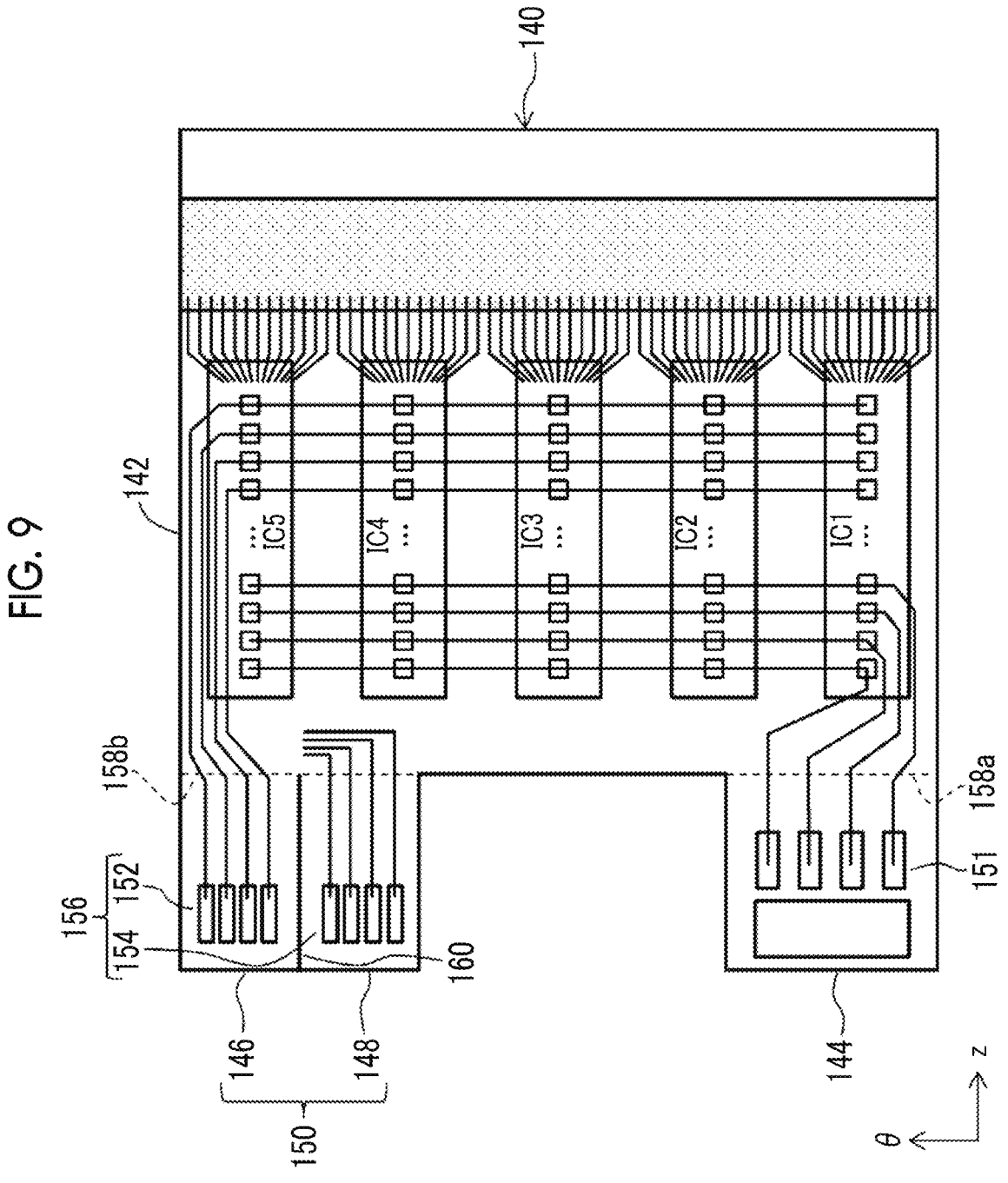
FIG. 9 is a developed view of a fifth example of the flexible substrate.

FIG. 9 shows a fifth example of the flexible substrate. A flexible substrate 140 includes a substrate main body 142, a first tab 144, a second tab 146, and a third tab 148. The first tab 144 is connected to one end part of the substrate main body 142, and the second tab 146 and the third tab 148 are connected to the other end part of the substrate main body 142. The second tab 146 and the third tab 148 constitute a tab pair 150. The tab pair 150 corresponds to the second tab shown in FIG. 3. A slit 160 is provided between the second tab 146 and the third tab 148.

The first tab 144 is provided with a first connection 151. The second tab 146 is provided with a second connection 152. The third tab 148 is provided with a third connection 154. The second connection 152 and the third connection 154 constitute a connection pair 156. The connection pair 156 corresponds to the second connection 64 shown in FIG. 3. In FIG. 9, a reference numeral 158*a* indicates a boundary between the first tab 144 and the substrate main body 142, and the boundary 158*a* corresponds to a bending line. A reference numeral 158*b* indicates a boundary between the tab pair 150 and the substrate main body 142, and the boundary 158*b* corresponds to a bending line.

According to the fifth example shown in FIG. 9, it is possible to reduce the widths of the tabs 146 and 148 in the θ direction. Accordingly, it is easy to bend the tabs 146 and 148 at the time of probe assembly. In general, the number of tabs is 2 or 3.

What is claimed is:

1. An intracavitary insertion type ultrasound probe comprising:
 a flexible substrate including a substrate main body that is rolled into a tubular shape and a plurality of tabs that are connected to a rear end of the substrate main body, the substrate main body having a rectangular form in a development state of the flexible substrate, and the rear end being a rear side of the rectangular form in the development state;
 an annular transducer array that is provided on the substrate main body; and
 a plurality of electronic components that are provided on the substrate main body, are electrically connected to the transducer array, and are disposed side by side annularly, wherein one end and the other end of the substrate main body in a circumferential direction are in contact with or close to each other, the substrate main body includes one end part including the one end and the other end part including the other end, the one end part and the other end part are separated from each other in the circumferential direction, the plurality of tabs include a first tab connected to the one end part and a second tab connected to the other end part, the first tab is provided with a first connection to which a first cable group is connected, the second tab is provided with a second connection to which a second cable group is connected, and the flexible substrate further includes a first cross line array that extends from the one end part to the other end part and is electrically connected to the plurality of electronic components, a second cross line array that extends from the other end part to the one end part and is electrically connected to the plurality of electronic components, a first peripheral line array provided between the first cross line array and the first connection, and a second peripheral line array provided between the second cross line array and the second connection, and wherein the first cross line array and the second cross line array are separated from each other in a z direction which is parallel to a probe central axis, the first peripheral line array is connected to the first cross line array in the one end part, and the second peripheral line array is connected to the second cross line array in the other end part.

2. The intracavitary insertion type ultrasound probe according to claim 1, wherein the first cross line array and the first peripheral line array each include a plurality of lines for transmitting a plurality of reception signals, and the second cross line array and the second peripheral line array each include a line for transmitting a control signal and a line for supplying a power voltage.

3. The intracavitary insertion type ultrasound probe according to claim 2, wherein the flexible substrate has a ground line provided between the first connection and the second connection.

4. The intracavitary insertion type ultrasound probe according to claim 2, wherein the first tab has a ground line surrounding the first connection.

5. The intracavitary insertion type ultrasound probe according to claim 1, wherein the substrate main body includes a first region provided with the transducer array, a second region provided on a rear side of the first region and provided with the plurality of electronic components, and a third region between the second region and the rear end, and wherein each of the tabs extends in parallel to a probe central axis direction in a normal state, and the third region is deformed in a case where a pressing force is applied to each of the tabs toward an outer side in a radial direction, and thus each of the tabs is allowed to be bent.

6. The intracavitary insertion type ultrasound probe according to claim 1, wherein at least one of the plurality of tabs includes a tab main body and a coupling part provided between the tab main body and the substrate main body, and a width of a boundary between the coupling part and the substrate main body is smaller than a width of the tab main body in a circumferential direction.

* * * * *